(12) United States Patent
Horstmeyer et al.

(10) Patent No.: US 10,420,498 B1
(45) Date of Patent: Sep. 24, 2019

(54) SPATIAL AND TEMPORAL-BASED DIFFUSIVE CORRELATION SPECTROSCOPY SYSTEMS AND METHODS

(71) Applicant: HI LLC, Los Angeles, CA (US)

(72) Inventors: Roarke Horstmeyer, Durham, NC (US); Haojiang Zhou, Los Angeles, CA (US); Yuecheng Shen, Guangzhou University (CN); Haowen Ruan, Pasadena, CA (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 16/226,625

(22) Filed: Dec. 19, 2018

Related U.S. Application Data

(60) Provisional application No. 62/687,657, filed on Jun. 20, 2018, provisional application No. 62/717,664, filed on Aug. 10, 2018.

(51) Int. Cl.
*A61B 5/00* (2006.01)
*A61B 5/026* (2006.01)
(Continued)

(52) U.S. Cl.
CPC .......... *A61B 5/4064* (2013.01); *A61B 5/0075* (2013.01); *A61B 5/029* (2013.01);
(Continued)

(58) Field of Classification Search
CPC ... A61B 5/4064; A61B 5/0075; A61B 5/0261; A61B 5/029; A61B 5/0402;
(Continued)

(56) References Cited

U.S. PATENT DOCUMENTS 5,528,365 A 6/1996 Gonatas et al.
5,983,120 A * 11/1999 Groner ................ A61B 5/0261
356/364
(Continued)

FOREIGN PATENT DOCUMENTS

EP 0656536 4/2004
WO 2015/109005 7/2015
(Continued)

OTHER PUBLICATIONS

Hebert, Benedict, Santiago Costantino, and Paul W. Wiseman. "Spatiotemporal image correlation spectroscopy (STICS) theory, verification, and application to protein velocity mapping in living CHO cells." Biophysical journal 88, No. 5 (2005): 3601-3614.*
(Continued)

*Primary Examiner* — Carolyn A Pehlke
(74) *Attorney, Agent, or Firm* — ALG Intellectual Property, LLC

(57) ABSTRACT

A system includes a photodetector array and a processor. The photodetector array includes a plurality of photodetectors and is configured to detect light that exits a body and output a plurality of electronic signals representative of the detected light as a function of time. The processor is configured to sample the electronic signals output by the photodetector array at a plurality of delay times during a predetermined time period to generate a sequence of frames, apply a plurality of temporal-based and spatial-based correlation measurement operations to sample values in each of the frames, generate, based on the application of the temporal-based and spatial-based correlation measurement operations to the sample values in each of the frames, a plurality of spatiotemporal correlation measure values for the light detected by the photodetector array, and include the
(Continued)

plurality of spatiotemporal correlation measure values in a correlation map.

28 Claims, 13 Drawing Sheets

(51) Int. Cl.
    *A61B 5/0402*         (2006.01)
    *A61B 5/0476*         (2006.01)
    *A61B 5/029*          (2006.01)

(52) U.S. Cl.
    CPC .......... *A61B 5/0261* (2013.01); *A61B 5/0402* (2013.01); *A61B 5/0476* (2013.01); *A61B 5/6814* (2013.01); *A61B 5/7246* (2013.01)

(58) Field of Classification Search
    CPC ... A61B 5/0476; A61B 5/6814; A61B 5/7246; A61B 5/14553; A61B 5/72; A61B 2562/0238; G06F 3/015; G06F 3/01; G06F 17/10; G06F 19/30; G01J 3/10; G01J 3/2889; G01J 3/4406; G01N 21/4795; G01N 21/64
    See application file for complete search history.

(56) References Cited

U.S. PATENT DOCUMENTS

| | | | |
|---|---|---|---|
| 8,082,015 | B2 | 12/2011 | Yodh et al. |
| 9,157,858 | B2 | 10/2015 | Claps |
| 9,946,344 | B2 | 4/2018 | Ayaz et al. |
| 2010/0210952 | A1* | 8/2010 | Taira ............... A61B 1/043 600/476 |
| 2015/0182136 | A1* | 7/2015 | Durduran ........ G01B 9/02094 600/425 |
| 2016/0345880 | A1 | 12/2016 | Nakaji et al. |
| 2018/0070830 | A1 | 3/2018 | Sutin et al. |
| 2018/0070831 | A1 | 3/2018 | Sutin et al. |
| 2018/0089531 | A1 | 3/2018 | Geva et al. |
| 2018/0103861 | A1 | 4/2018 | Sutin et al. |
| 2018/0185667 | A1 | 7/2018 | Huang |

FOREIGN PATENT DOCUMENTS

| | | |
|---|---|---|
| WO | 2016/164900 | 10/2016 |
| WO | 2017/147539 | 8/2017 |
| WO | 2018/090040 | 5/2018 |

OTHER PUBLICATIONS

Leow Wee Kheng (Image Processing, https://www.comp.nus.edu.sg/~cs4243/lecture/imageproc.pdf, Mar. 9, 2014).*

Sneha (Understanding Correlation, https://www.allaboutcircuits.com/technical-articles/understanding-correlation/, Jan. 4, 2017).*

Alan Zucconi (The Autocorrelation Function, https://www.alanzucconi.com/2016/06/06/autocorrelation-function/, Jun. 6, 2016).*

Boas, et al.,Establishing the diffuse correlation spectroscopy signal relationship with blood flow, Neurophotonics, 3(3), 031412 (2016), www.Neurophotonics.SPIEDigitalLibrary.org, 2016,1-9.

SPC3 Single Photon Counting Camera, Micro Photon Devices S.r.l. SPC3 User Manual Version 1.1.0—Nov. 2015.

BOAS,D. A. et al., Scattering and Imaging with Diffusing Temporal Field Correlations, The American Physical Society. Physical Review Letters, vol. 75, No. 9, Aug. 28, 1995.

Buckley,Erin M. et al., Diffuse correlation spectroscopy for measurement of cerebral blood flow: future prospects, Neurophotonics vol. 1(1), 011009 (Jul.-Sep. 2014). https://www.spiedigitallibrary.org/journals/Neurophotonics.

Dietsche,G. et al., Fiber-based multispeckle detection for time-resolved diffusing-wave spectroscopy: characterization and application to blood flow detection in deep tissue, Applied Optics 46 (2007), 35, pp. 8506-8514.

Li,Jun et al., Pulsation-resolved deep tissue dynamics measured with diffusing-wave spectroscopy, Aug. 21, 2006 / vol. 14, No. 17 / Optics Express 7841.

Pagliazzi,M. et al., Time domain diffuse correlation spectroscopy with a high coherence pulsed source: in vivo and phantom results, vol. 8, No. 11 / Nov. 1, 2017 / Biomedical Optics Express 5311.

Sutin,Jason et al., Time-domain diffuse correlation spectroscopy, vol. 3, No. 9 / Sep. 2016 / Optica 1006-1013.

Wang,Detian et al., Fast blood flow monitoring in deep tissues with real-time software correlators, Optical Society of America, Mar. 1, 2016 / vol. 7, No. 3 / DOI:10.1364/BOE7.000776 / Biomedical Optics Express 776.

Zarychta,Katarzyna et al., Time-resolved diffusing wave spectroscopy with a CCD camera, Aug. 2, 2010 / vol. 18, No. 16 / Optics Express 16289.

Zhou,Chao et al., Diffuse optical correlation tomography of cerebral blood flow during cortical spreading depression in rat brain, Optical Society of America, Feb. 6, 2006 / vol. 14, No. 3 / Optics Express 1125.

\* cited by examiner

SPATIAL AND TEMPORAL-BASED DIFFUSIVE CORRELATION SPECTROSCOPY SYSTEMS AND METHODS

RELATED APPLICATIONS

The present application claims priority under 35 U.S.C. § 119(e) to U.S. Provisional Patent Application No. 62/687,657, filed on Jun. 20, 2018, and to U.S. Provisional Patent Application No. 62/717,664, filed on Aug. 10, 2018. These applications are incorporated herein by reference in their respective entireties.

BACKGROUND INFORMATION

Detection of brain activity is useful for medical diagnostics, imaging, neuroengineering, brain-computer interfacing, and a variety of other diagnostic and consumer-related applications. For example, cerebral blood flow ensures the delivery of oxygen and needed substrates to tissue, as well as removal of metabolic waste products. Thus, detection and quantification of cerebral blood flow is useful for diagnosis and management of any brain injury or disease associated with ischemia or inadequate vascular autoregulation.

As another example, there is an increasing interest in measuring event-related optical signals (also referred to as fast-optical signals). Such signals are caused by changes in optical scattering that occur when light propagating through active neural tissue (e.g., active brain tissue) is perturbed through a variety of mechanisms, including, but not limited to, cell swelling, cell volume change, cell displacement, changes in membrane potential, changes in membrane geometry, ion redistribution, birefringence changes, etc. Because event-related optical signals are associated with neuronal activity, rather than hemodynamic responses, they may be used to detect brain activity with relatively high temporal resolution, Diffusive correlation spectroscopy (DCS), also referred to as diffusive wave spectroscopy (DWS), is a non-invasive optical procedure that has been shown to be effective in measuring some types of brain activity, such as cerebral blood flow. A conventional DCS system directs high coherence light (e.g., a laser) at a head of a subject. Some of the light propagates through the scalp and skull and into the brain where it is scattered by moving red blood cells in tissue vasculature before exiting the head. This dynamic scattering from moving cells causes the intensity of the light that exits the head to temporally fluctuate. To detect these temporal fluctuations, a conventional DCS system includes a photodetector and a correlator. The photodetector detects individual photons in the light that exits the head. The correlator keeps track of the arrival times of all photons detected by the photodetector and derives an intensity correlation function from temporal separations between the photons. This intensity correlation function is representative of the temporal fluctuations of the intensity of the light that exits the head, and is therefore also indicative of blood flow.

A conventional photodetector requires approximately one second to acquire enough signal for a meaningful measurement by a conventional DCS system. This is sufficient to detect changes in blood flow, which occur at relatively slow time scales (e.g., one second or more). However, conventional DCS systems do not operate fast enough to detect event-related optical signals caused, for example, by cellular activity, which occurs at a much faster rate than changes in blood flow.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
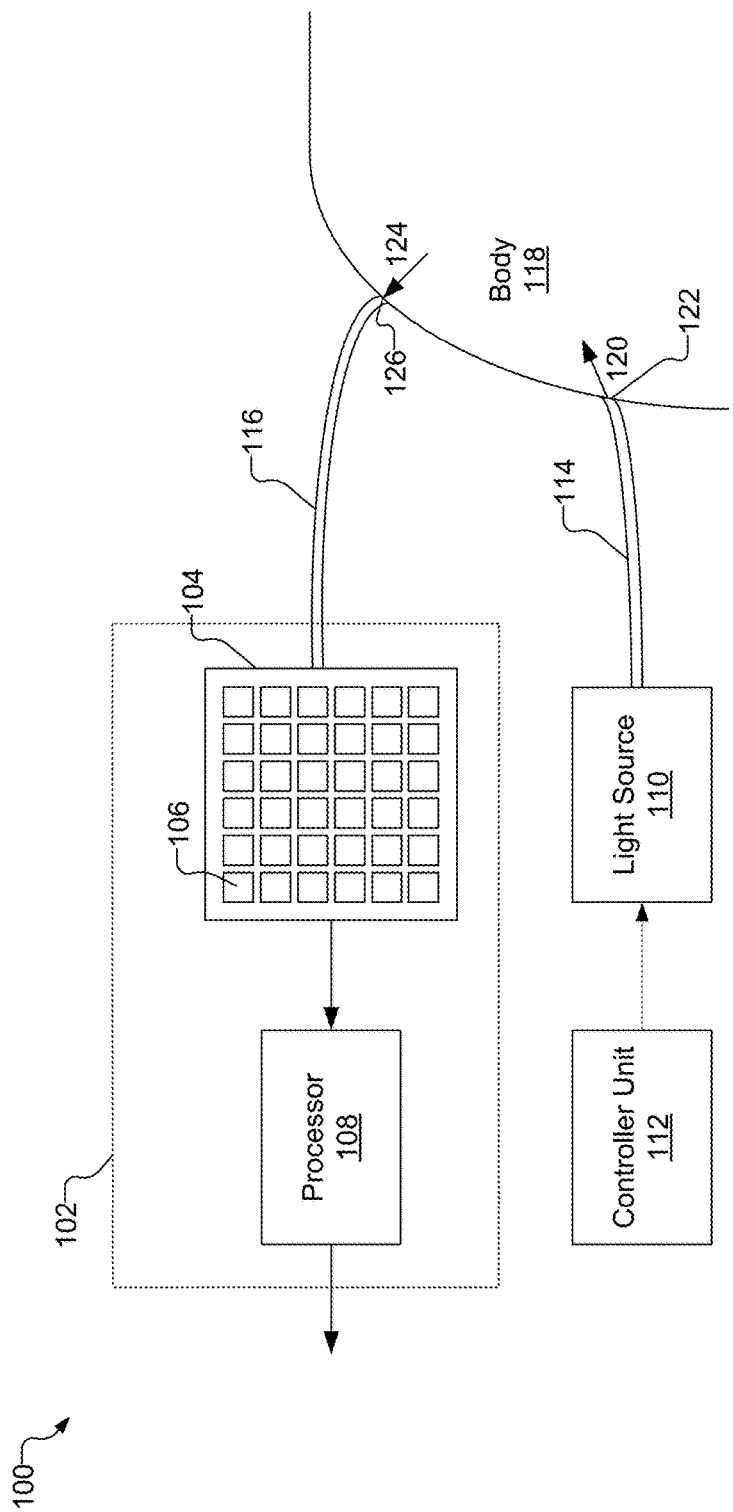
FIG. 1 shows an exemplary configuration in which a DCS system is configured to determine spatiotemporal correlation measurement values according to principles described herein.

Spatial and temporal-based DCS systems and methods are described herein. In some examples, as will be described in more detail below, a light source (e.g., a laser diode) generates coherent light that enters a body (e.g., a head of a subject) at an input location. The incident light scatters through many different optical paths within the body. Because of its high coherence, the light emerges from the body with the ability to interfere with itself to produce an interference pattern at one or more output locations. This interference pattern takes the form of a fully developed speckle pattern at the one or more output locations. A DCS system as described herein may determine spatiotemporal correlation measurement values representative of speckle decorrelation (i.e., how speckles within the speckle pattern vary with respect to time and space).

To this end, the DCS system includes a K by L photodetector array and a processor coupled to an output of the photodetector array. The photodetector array includes a plurality of photodetectors each configured to detect light that emerges from the body after it has scattered within the body. Each photodetector is further configured to output an electronic signal representative of the detected light as a function of time. Hence, the photodetector array as a whole is configured to output a plurality of electronic signals representative of the detected light as a function of time.

The processor is configured to sample the electronic signals output by the photodetector array at a plurality of delay times during a predetermined time period to generate a sequence of frames each corresponding to a different delay time in the plurality of delay times. Each of the frames includes K times L digital sample values at K by L pixel locations that correspond to locations of the photodetectors within the photodetector array.

The processor is further configured to apply a plurality of temporal-based and spatial-based correlation measurement operations to the sample values in each of the frames. Based on the application of the temporal-based and spatial-based correlation measurement operations to the sample values, the processor is configured to generate a plurality of spatiotemporal correlation measure values for the light detected by the photodetector array. These spatiotemporal correlation measure values represent speckle decorrelation associated with the light detected by the photodetector array. The processor is further configured to include the plurality of spatiotemporal correlation measure values in a correlation map that corresponds to a predetermined delay time interval. The predetermined delay time interval represents a difference between two delay times within the plurality of delay times.

By applying both temporal-based and spatial-based correlation measurement operations, as opposed to only temporal-based measurement operations as applied in conventional DCS systems, the systems and methods described herein provide additional useful information regarding the decorrelation process of coherent light that exits the body after scattering within the body. For example, the spatiotemporal correlation measure values generated by the systems and methods described herein may provide more accurate, useful, and distinguishing measures of brain activity than correlation measures generated by conventional DCS systems that are only temporally based.

Moreover, by applying both temporal-based and spatial-based correlation measurement operations, the systems and methods described herein can relax sampling requirements over time. For example, decorrelation rates in the human head typically require sampling at 1 MHz when only temporal-based correlation measurement operations are performed. However, by also performing spatial-based correlation measurement operations, the systems and methods described herein can obtain accurate measurements of decorrelation at sample rates that are much lower (e.g., around 200 kHz).

Furthermore, by using a photodetector array that includes many (e.g., 100 to 100,000) photodetectors, as opposed to a single photodetector as used in conventional DCS systems, the systems and methods described herein can dramatically speed up the sampling rate of DCS into the sub-millisecond range. By speeding up acquisition into this range, the systems and methods described herein can sample at rates that are sufficient to resolve event-related optical signals (also referred to as fast-optical signals). Such signals are caused by changes in optical scattering that occur when light propagating through active neural tissue (e.g., active brain tissue) is perturbed through a variety of mechanisms, including, but not limited to, cell swelling, cell volume change, cell displacement, changes in membrane potential, changes in membrane geometry, ion redistribution, birefringence changes, etc. Because event-related optical signals are associated with neuronal activity, rather than hemodynamic responses, they may be used to detect brain activity with relatively high temporal resolution. Resolution of event-related optical signals is described more fully in U.S. Provisional Application No. 62/692,074, filed Jun. 29, 2018, the contents of which are hereby incorporated by reference in their entirety.

These and other benefits and/or advantages that may be provided by the systems and methods described herein will be made apparent by the following detailed description.

FIG. 1 shows an exemplary configuration 100 in which a DCS system 102 is configured to determine spatiotemporal correlation measurement values representative of speckle decorrelation. As shown, DCS system 102 includes a photodetector array 104 composed of a plurality of individual photodetectors (e.g., photodetector 106) and a processor 108 coupled to an output of photodetector array 104. Other components included in configuration 100 (e.g., a light source 110, a controller unit 112, and optical fibers 114 and 116) are not shown to be included in DCS system 102 in FIG. 1. However, one or more of these components may, in certain embodiments, be considered to be a part of DCS system 102.

Light source 110 may be implemented by any suitable component configured to generate and emit high coherence light (e.g., light that has a coherence length of at least 5 centimeters) at a predetermined center wavelength. For example, light source 110 may be implemented by a high-coherence laser diode.

Light source 110 is controlled by controller unit 112, which may be implemented by any suitable computing device, integrated circuit, and/or combination of hardware and/or software as may serve a particular implementation. In some examples, controller unit 112 is configured to control light source 110 by turning light source 110 on and off and/or setting an intensity of light generated by light source 110. Controller unit 112 may be manually operated by a user, or may be programmed to control light source 110 automatically.

Light emitted by light source 110 travels via an optical fiber 114 (e.g., a single-mode fiber or a multi-mode fiber) to a body 118 of a subject. In some implementations, body 118 is a head or any other body part of a human or other animal. Alternatively, body 118 may be a non-living object. For illustrative purposes, it will be assumed in the examples provided herein that body 118 is a human head.

As indicated by arrow 120, the light emitted by light source 110 enters body 118 at a first location 122 on body 118. To this end, a distal end of fiber 114 may be positioned at (e.g., right above or physically attached to) first location 122 (e.g., to a scalp of the subject). In some examples, the light may emerge from fiber 114 and spread out to a certain spot size on body 118 to fall under a predetermined safety limit.

After the light enters body 118, the light scatters through many different optical paths within body 118. The light emerges from body 118 at various locations. For example, as illustrated by arrow 124, the light may exit from body 118 at location 126, which is different than location 122. Because of its high coherence, the light may interfere with itself to produce an interference pattern in the form of a fully developed speckle pattern at location 126.

As shown, a proximal end of optical fiber 116 (e.g., a multi-mode optical fiber) is positioned at (e.g., right above or physically attached to) output location 126. In this manner, optical fiber 116 may collect light as it exits body 124 at location 126 and carry the light to photodetector array 104. The light may pass through one or more lenses and/or other optical elements (not shown) that direct the light onto each of the photodetectors 106 included in photodetector array 104.

Figure 2:
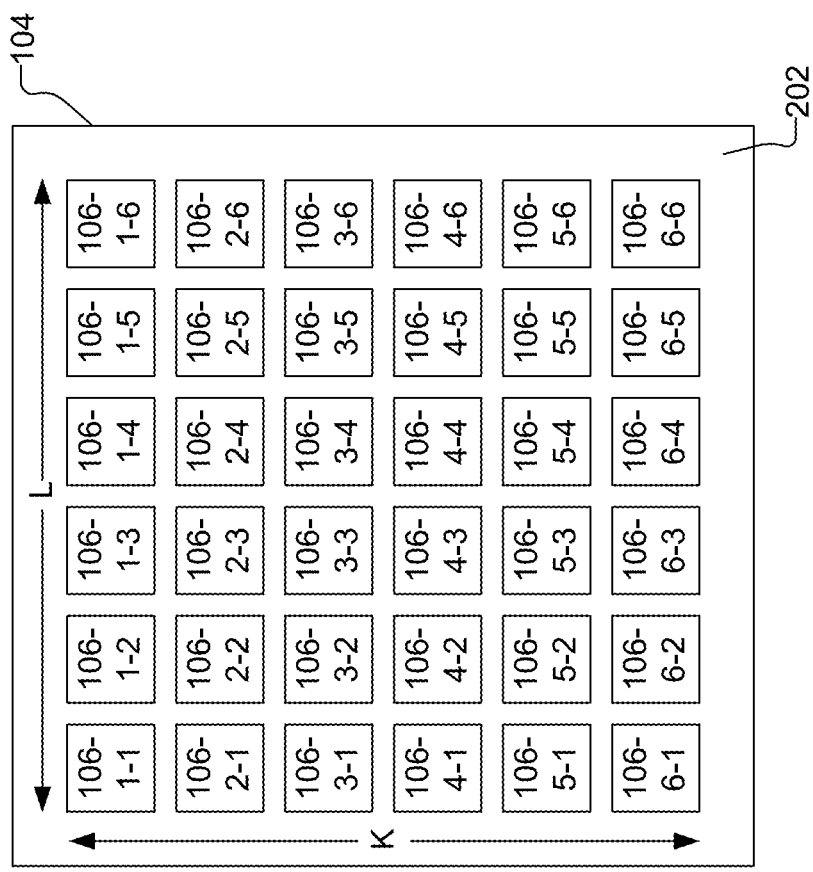
FIG. 2 illustrates an exemplary photodetector array according to principles described herein.

FIG. 2 illustrates photodetector array 104 in more detail. As shown, photodetector array includes a plurality of photodetectors 106 arranged in a K by L array. In the example of FIG. 2, K and L are both equal to six. However, it will be recognized that photodetector array 104 may have any other suitable dimension where K times L is greater than one. In some examples, photodetector array 104 includes between 10 and 100,000 photodetectors.

Each photodetector 106 is labeled in FIG. 2 with indices that indicate a position (i.e., a row number and a column number) of the photodetector within photodetector array 104. For example, photodetector 106-1-1 is located in the first row and first column of photodetector array 104 and photodetector 106-6-6 is located in the sixth row and sixth column of photodetector array 104. As shown, each photodetector 106 may be disposed on a surface 202. Surface 202 may be implemented by a printed circuit board (PCB), an ASIC, or any other suitable surface. In some examples, each photodetector 106 may be created via lithography on a silicon substrate, and then wire-bonded and packaged like other similar CMOS image chips.

Photodetectors 106 may each be implemented by any suitable circuit configured to detect individual photons of light incident upon photodetectors 106. For example, each photodetector 106 may be implemented by a single photon avalanche diode (SPAD) circuit. Unlike conventional SPAD circuits, the SPAD circuits that implement photodetectors 106 operate in a freely-running configuration, as opposed to a time-correlated single-photon-counting configuration.

Photodetectors 106 may each detect light that exits the body at location 126 and output an electronic signal representative of the detected light as a function of time. Because there are K times L photodetectors 106, photodetector array 104 outputs K times L electronic signals, where each photodetector 106 generates a different one of the K times L electronic signals.

To illustrate, a photodetector (e.g., photodetector 106-1-1) may detect light and output an electronic signal representative of the detected light as a function of time by detecting individual photons as they arrive at the photodetector and outputting an analog pulse each time a photon is detected. Hence, the electronic signal may include a series of pulses, where each pulse represents an arrival time of a photon. Alternatively, the photodetector may track how many photons arrive at the photodetector during a particular time interval (e.g., 10 microseconds) and output a count value representative of this number. In this case, the electronic signal output by the photodetector may include a series of values each representative of a number of photons that hit the photodetector during subsequent time intervals.

Photodetectors 106 may be configured to operate in a freely running mode as opposed to a time-correlated single photon counting mode. In other words, the photodetectors 106 used in connection with the systems and methods described herein may simply output pulses when photons are detected without having to determine actual arrival times of the photons. This advantageously reduces the complexity and cost of the photodetectors 106 compared to conventional DCS systems that use time-of-flight optical measurement systems for in-vivo detection.

Processor 108 may be implemented by one or more physical processing (e.g., computing) devices. In some examples, processor 108 may execute software configured to perform one or more of the operations described herein. Processor 108 is configured to sample the electronic signals output by photodetector array 104 at N delay times during a time period T to generate a sequence of N frames. The time period T may be of any suitable duration (e.g., less than or equal to one microsecond). N may also have any suitable value greater than one. For example, N may be between 10 and 100,000.

Figure 3:
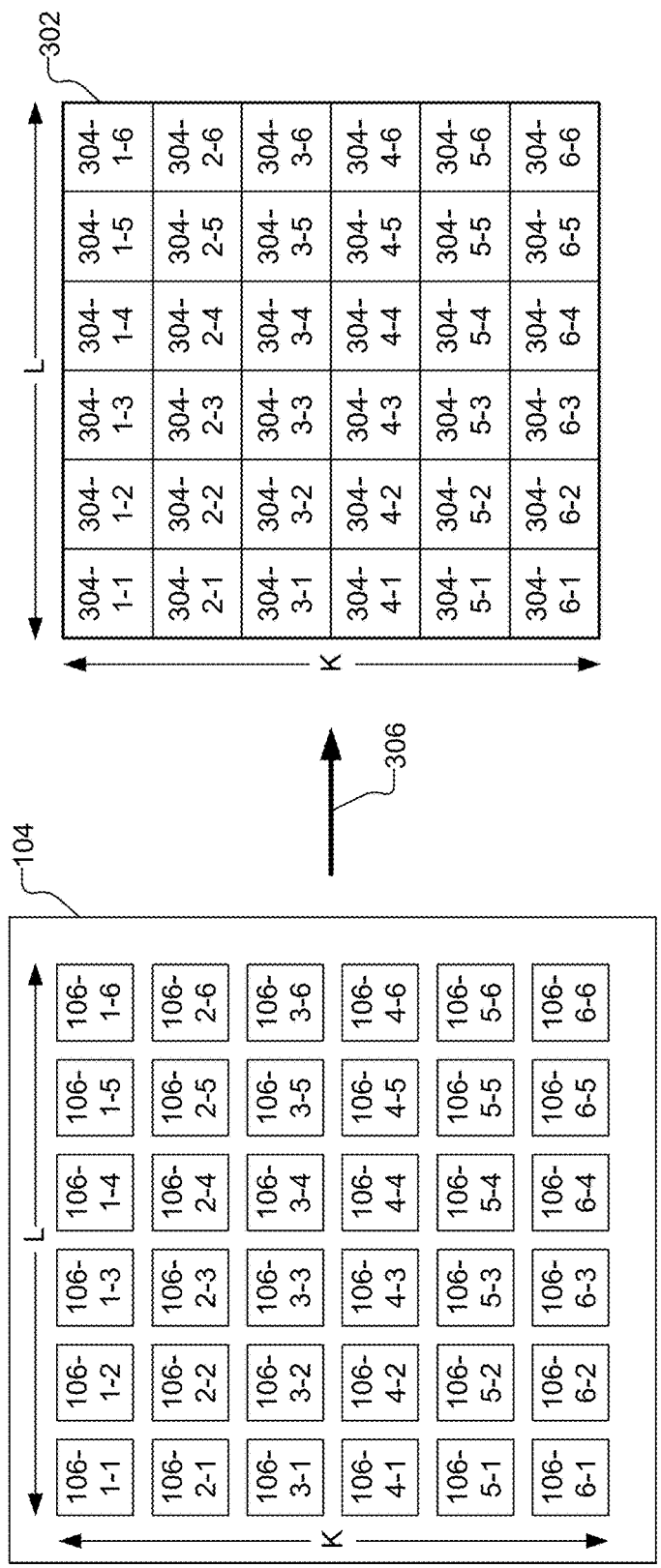
FIG. 3 shows a relationship between a photodetector array and a frame according to principles described herein.

FIG. 3 shows a relationship between photodetector array 104 and a frame 302 included in the N frames generated by processor 108 sampling the electronic signals output by photodetector array 104 at a particular delay time. Each of the N frames generated by processor 108 has the same dimensions and structure as frame 302.

As shown, frame 302 has K by L pixel locations 304. Each pixel location 304 is labeled in FIG. 3 with indices that indicate a position (i.e., a row number and a column number) of the pixel location 304 within frame 302. For example, pixel location 304-1-1 is located in the first row and first column of frame 302 and pixel location 304-6-6 is located in the sixth row and sixth column of frame 302. Each pixel location 304 corresponds to a location of a particular photodetector 106 in photodetector array 104. For example, pixel location 304-1-1 corresponds to a location of photodetector 106-1-1 in photodetector array 104, pixel location 304-1-2 corresponds to a location of photodetector 106-1-2 in photodetector array 104, etc.

As mentioned, frame 302 is generated by processor 108 sampling the electronic signals output by photodetector array 104 at a particular delay time. This sampling is represented in FIG. 3 by arrow 306 and may be performed in accordance with any suitable signal processing heuristic. The sampling generates a plurality of digital sample values that are included in frame 302 at pixel locations 304. For example, frame 302 includes a digital sample value at pixel location 304-1-1 of an electronic signal output by photodetector 106-1-1, a digital sample value at pixel location 304-1-2 of an electronic signal output by photodetector 106-1-2, etc.

Processor 108 may apply a plurality of temporal-based and spatial-based correlation measurement operations to the sample values in each of the N frames generated by processor 108. Based on the application of the temporal-based and spatial-based correlation measurement operations to the sample values, processor 108 may generate a plurality of spatiotemporal correlation measure values for the light detected by photodetector array 104. Processor 108 may include the plurality of spatiotemporal correlation measure values in one or more correlation maps that each corresponding to a different predetermined delay time interval.

Figure 4:
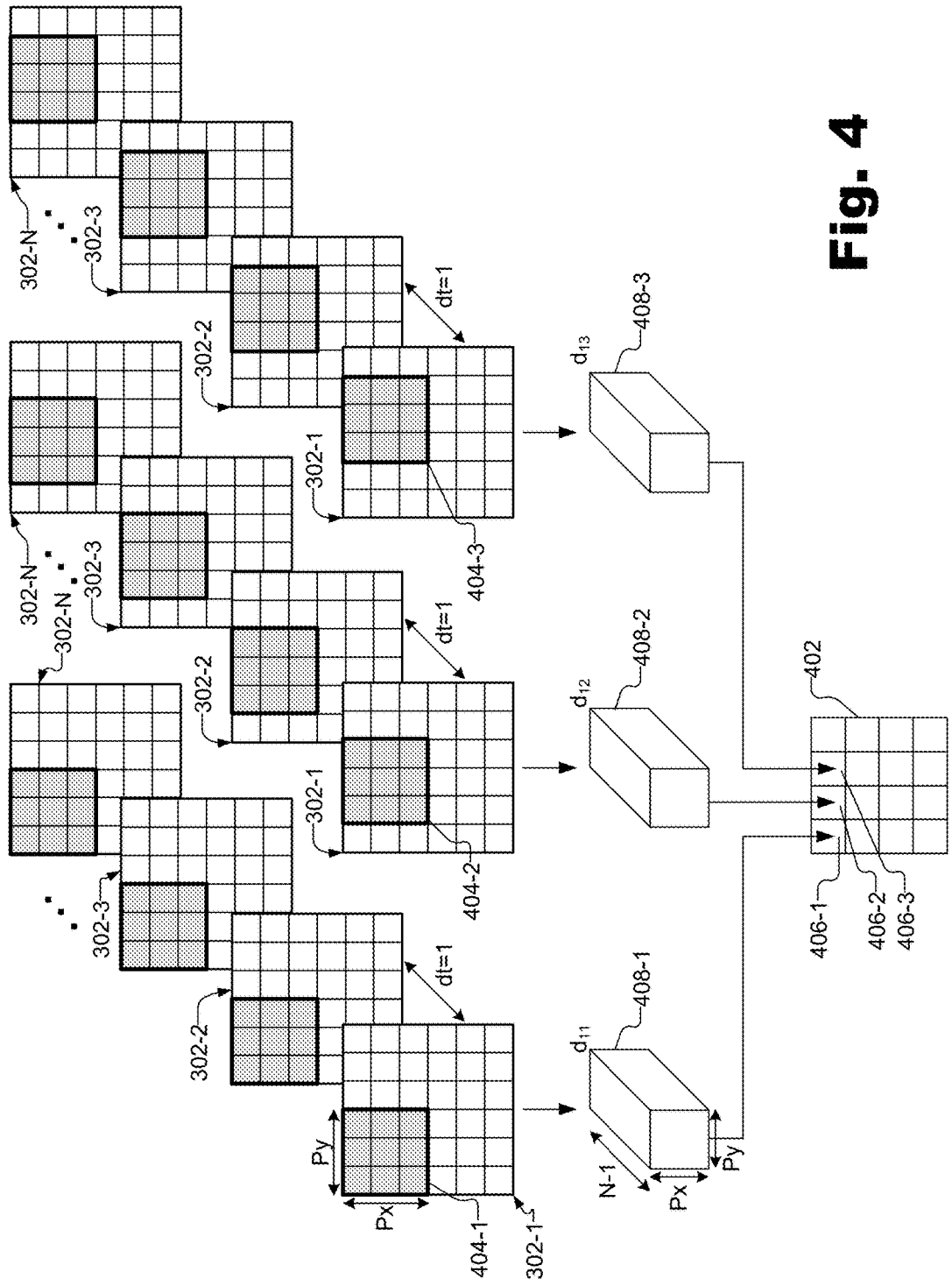
FIG. 4 illustrates an exemplary heuristic that may be performed by a processor on a sequence of frames to generate a correlation map according to principles described herein.

FIG. 4 illustrates an exemplary heuristic that may be performed by processor 108 on a sequence of frames 302 to generate a correlation map 402 that corresponds to a delay time interval of one, where the delay time interval is defined as an integer number of delay times between frames, from which frames will be considered to generate a particular correlation measurement. As shown, the sequence of frames 302 includes frames 302-1 through 302-N. Each frame 302 is generated by processor 108 sampling the electronic signals output by photodetector array 104 at a particular delay time. For example, frame 302-1 is generated by processor 108 sampling the electronic signals output by photodetector array 104 at a first delay time, frame 302-2 is generated by processor 108 sampling the electronic signals output by photodetector array 104 at a second delay time immediately subsequent to the first delay time, etc. Each frame 302 is therefore temporally spaced from a subsequent frame 302 by a delay time interval (dt) of one (i.e., dt=1). The same sequence of frames 302 is shown three different times in FIG. 4 to illustrate how frames 302 are processed by processor 108, as will be made apparent below.

In the example of FIG. 4, processor 108 generates correlation map 402 by applying a plurality of temporal-based and spatial-based correlation measurement operations to sample values included in a plurality of overlapping pixel regions (e.g., pixel regions 304-1 through 304-3). The overlapping pixel regions 304 are shaded and surrounded by a thick border for illustrative purposes. In the particular example of FIG. 4, each pixel region 404 includes a three by three block of pixel locations. For example, pixel region 404-1 includes pixel locations in the top-left corner of frame 302-1. With reference to FIG. 3, these pixel locations include pixel locations 304-1-1, 304-1-2, 304-1-3, 304-2-1, 304-2-2, 304-2-3, 304-3-1, 304-3-2, and 304-3-3. As shown, pixel region 404-2 overlaps with and is offset from pixel region 404-1 by one pixel column to the right. Likewise, pixel region 404-3 overlaps with and is offset from pixel region 404-2 by one pixel column to the right. Other pixel regions of the same size (e.g., a pixel region that overlaps with and is offset from pixel region 404-1 by one row down) are not specifically highlighted in FIG. 4. However, it will be recognized that in the example of FIG. 4, sixteen three by three pixel regions fit within each of frames 302.

It will be recognized that while three by three pixel regions are shown in FIG. 4, the pixel regions may alternatively be of any other suitable size. In general, each pixel region may include Px by Py pixel locations, where Px times Py is greater than one.

Correlation map 402 includes a plurality of locations 406 (e.g., locations 406-1 through 406-3) that each correspond to a particular one of the overlapping pixel regions 404 (i.e., each location 406 includes a spatiotemporal correlation measure value corresponding to one of the overlapping pixel regions 404). For example, in the example of FIG. 4, location 406-1 corresponds to pixel region 404-1, location 406-2 corresponds to pixel region 404-2, and location 406-3 corresponds to pixel region 404-3. Hence, the size of correlation map 402 depends on the number of overlapping pixel regions 404 included in each frame 302. In the example of FIG. 4, because there are a total of sixteen possible overlapping pixel regions 404 in frames 302, correlation map 402 may include sixteen locations 406, arranged in a four by four matrix.

Exemplary temporal-based and spatial-based correlation measurement operations that may be performed by processor 108 with respect to pixel region 404-1 will now be described. Because correlation map 402 corresponds to a delay time interval of one, processor 108 may first apply a plurality of temporal-based correlation measurement operations to sample values included in corresponding pixel locations within pixel region 404-1 for each subsequent and overlapping pair of frames 302 (i.e., frames 302-1 and 302-2, frames 302-2 and 302-3, etc.).

Figure 5:
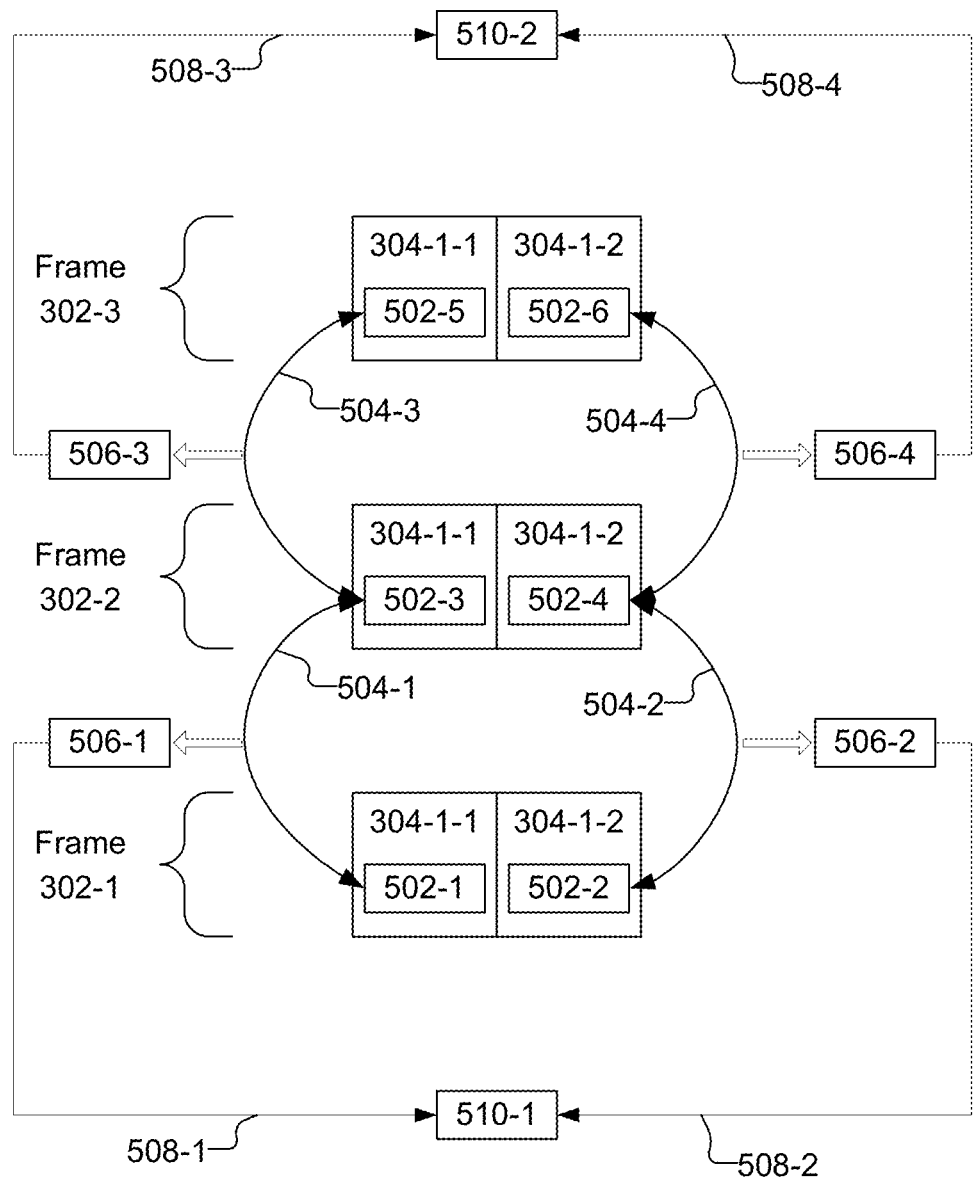
FIG. 5 shows pixel locations included in a pixel region of a frame according to principles described herein.

To illustrate, FIG. 5 shows pixel locations 304-1-1 and 304-1-2 included in pixel region 404-1 of each of frames 302-1 through 302-3. Only two of the nine pixel locations of pixel region 404-1 are shown in FIG. 5 for illustrative purposes. As shown, frames 302 each include a sample value 502 at each of pixel locations 304-1-1 and 304-1-2. For example, frame 302-1 includes a sample value 502-1 at pixel location 304-1-1 and a sample value 502-2 at pixel location 304-1-2, frame 302-2 includes a sample value 502-3 at pixel location 304-1-1 and a sample value 502-4 at pixel location 304-1-2, and frame 302-3 includes a sample value 502-5 at pixel location 304-1-1 and a sample value 502-6 at pixel location 304-1-2.

As represented by arrow 504-1, processor 108 may apply a first temporal-based correlation measurement operation to frames 302-1 and 302-2 by processing sample value 502-1 with sample value 502-3 to obtain a first temporal correlation measure value 506-1 for pixel location 304-1-1. Likewise, as represented by arrow 504-2, processor 108 may apply a second temporal-based correlation measurement operation to frames 302-1 and 302-2 by processing sample value 502-2 with sample value 502-4 to obtain a temporal correlation measure value 506-2 for pixel location 304-1-2.

Processor 108 may similarly apply temporal-based correlation measurement operation to frames 302-2 and 302-3. For example, as represented by arrow 504-3, processor 108 may apply a first temporal-based correlation measurement operation to frames 302-2 and 302-3 by processing sample value 502-3 with sample value 502-5 to obtain a second temporal correlation measure value 506-3 for pixel location 304-1-1. Likewise, as represented by arrow 504-4, processor 108 may apply a second temporal-based correlation measurement operation to frames 302-2 and 302-3 by processing sample value 502-4 with sample value 502-6 to obtain a second temporal correlation measure value 506-4 for pixel location 304-1-2.

Processor 108 may similarly process sample values included in each of the other corresponding pixel locations included in pixel region 404-1 of frames 302-1 and 302-2, frames 302-2 and 302-3, etc. until processor 108 has obtained temporal correlation measurement values 506 for each pixel location of pixel region 404-1 in each subsequent and overlapping pair of frames 302.

Processor 108 may process a first sample value (e.g., sample value 502-1) with a second sample value (e.g., sample value 502-3) to obtain a temporal correlation measurement value (e.g., temporal correlation measurement value 506-1) in any suitable manner. For example, processor 108 may multiply the first sample value with the second sample value. Processor 108 may also process N different sample values in a repeated manner to obtain a temporal correlation measurement value. For example, processor 108 may multiply the first sample value with the second sample value, then multiply the second sample value with the third sample value, etc., and finally multiply the N−1th sample value with the Nth sample value, and then take the average of all of the N−1 products to obtain a temporal correlation measurement value. Example values of N may range from 10 to 10,000. Additional or alternative temporal-based correlation measurement operations may be performed on the first and second sample values, or on the N sample values, to obtain a temporal correlation measurement value as may serve a particular implementation.

With reference again to FIG. 4, processor 108 may include (e.g., store) the obtained temporal correlation measurement values 506 for each pixel location of pixel region 404-1 in a datacube 408-1 (also referred to as datacube $d_{11}$) corresponding to pixel region 404-1. As shown, datacube 408-1 is a three-dimensional array of temporal correlation measure values, and has dimensions of Px by Py by N−1. Datacube 408-1 may be conceptualized as having N−1 two-dimensional (2D) data matrices each having Px times Py temporal correlation measurement values 506. Each 2D data matrix in datacube 408-1 corresponds to a particular pairing of frames 302. For example, a first 2D data matrix in datacube 408-1 includes temporal correlation measurement values 506 generated based on sample values included in frames 302-1 and 302-2, a second 2D data matrix in datacube 408-1 includes temporal correlation measurement values 506 generated based on sample values included in frames 302-2 and 302-3, etc.

Processor 108 may similarly obtain and include temporal correlation measurement values 506 in datacubes for every other pixel region that fits within frames 302. For example, processor 108 may obtain temporal correlation measurement values 506 for pixel region 404-2, and include these temporal correlation measurement values 506 in a datacube 408-2 (also referred to as datacube $d_{12}$). Likewise, processor 108 may obtain temporal correlation measurement values 506 for pixel region 404-3, and include these temporal correlation measurement values 506 in a datacube 408-3 (also referred to as datacube $d_{13}$).

Processor 108 may apply spatial-based correlation measurement operations to the temporal correlation measurement values 506 included in each datacube 408. For example, with respect to datacube 408-1, processor 108 may apply the spatial-based correlation measurement operations by processing together all of the temporal correlation measurement values included in a particular 2D data matrix included in datacube 408-1.

To illustrate, reference is again made to FIG. 5. As illustrated by arrows 508-1 and 508-2, processor 108 may process temporal correlation measure value 506-1 with temporal correlation measure value 506-2 (and any other temporal correlation measure values obtained by processor 108 for the pair of frames 302-1 and 302-2) to obtain a first spatial correlation measure value 510-1. Likewise, as illustrated by arrows 508-3 and 508-4, processor 108 may process temporal correlation measure value 506-3 with temporal correlation measure value 506-4 (and any other temporal correlation measure values obtained by processor 108 for the pair of frames 302-2 and 302-3) to obtain a second spatial correlation measure value 510-2. This process may be repeated for each 2D data matrix included in datacube 408-1.

Processor 108 may process temporal correlation measure values 506 with each other in any suitable manner to obtain a spatial correlation measure value 510. For example, processor 108 may compute a variance of the temporal correlation measure values 506.

Processor 108 may combine each of the spatial correlation measure values generated for a datacube 408 into a single spatiotemporal correlation measure value for the pixel region 404 associated with the datacube 408. For example, processor 108 may combine spatial correlation measure value 510-1, spatial correlation measure value 510-2, and any other spatial correlation measure value obtained for pixel region 404-1 into a single spatiotemporal correlation measure value for pixel region 404-1. This combination may be performed in any suitable way. For example, processor 108 may add spatial correlation measure value 510-1, spatial correlation measure value 510-2, and any other spatial correlation measure value obtained for pixel region 404-1 together to obtain the single spatiotemporal correlation measure value for pixel region 404-1.

In general, the transformation of temporal correlation measure values in datacube 408-1 to a single spatiotemporal correlation measure value may be represented by $C[d_{11}, dt=1]$, where the function C can include any suitable processing operation. Likewise, the transformation of temporal correlation measure values in datacube 408-2 to a single spatiotemporal correlation measure value may be represented by $C[d_{12}, dt=1]$, the transformation of temporal correlation measure values in datacube 408-3 to a single spatiotemporal correlation measure value may be represented by $C[d_{13}, dt=1]$, etc. One exemplary function C is the sum of spatial variances over time, as describe above and as represented in the following equation: $C(d)=var[d[x,y,1)]+var[d[x,y,2)]+ \ldots +var[d[x,y,N-1)]$, where x and y refer the different pixel locations within a pixel region, and where the sum is over N different frames separated by a particular delay time interval.

The single spatiotemporal correlation measure values derived from datacubes 408 may be included by processor 108 in corresponding locations 406 in correlation map 402. For example, the single spatiotemporal correlation measure value derived from datacube 408-1 may be included in location 406-1, the single spatiotemporal correlation measure value derived from datacube 408-2 may be included in location 406-2, the single spatiotemporal correlation measure value derived from datacube 408-3 may be included in location 406-3, etc. This may be performed in any suitable manner.

Figure 6:
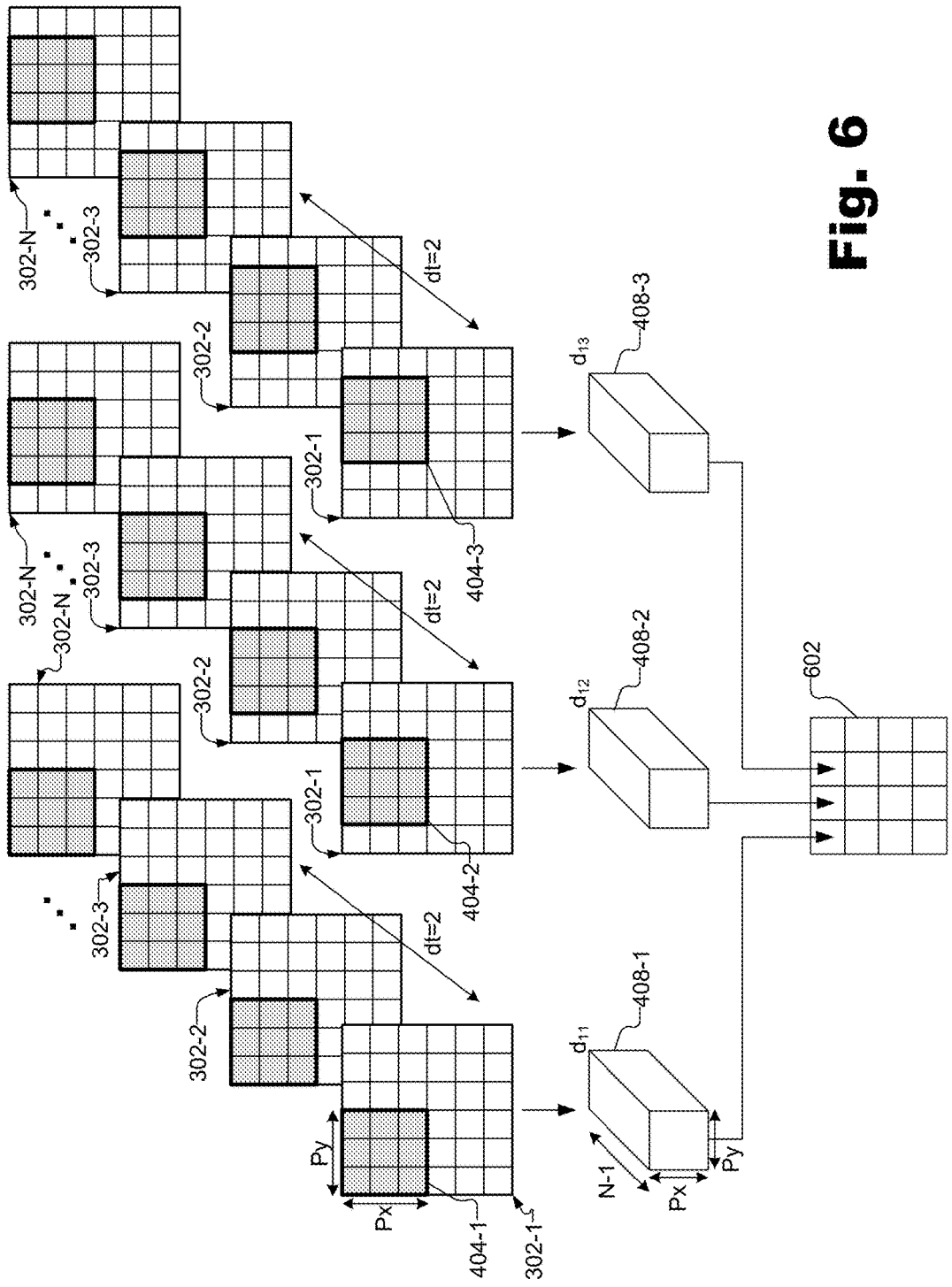
FIG. 6 illustrates an exemplary heuristic that may be performed by a processor on frames to generate a correlation map according to principles described herein.

The process described in FIG. 4 may be repeated for additional delay time intervals to generate additional correlation maps each corresponding to a different delay time interval. For example, FIG. 6 illustrates an exemplary heuristic that may be performed by processor 108 on frames 302 to generate a correlation map 602 that corresponds to a delay time interval of two. In this heuristic, processor 108 may apply temporal-based correlation measurement operations to pairs of frames 302 that are separated by a delay time interval of two (e.g., frames 302-1 and 302-3, frames 302-2 and 302-4 (not shown), etc.).

Any number of correlation maps may be generated by processor 108. For example, processor 108 may generate correlation maps corresponding to delay time intervals of dt=1, dt=2, dt=3, . . . , dt=G, where G may be any suitable number (e.g., between 10 and 1000). Here, G is analogous to the maximum temporal extent of a standard decorrelation curve in DCS. The correlation maps generated by processor 108 may be transmitted by processor 108 to any suitable computing device configured to process the data included in the correlation maps (e.g., by using the correlation maps to generate a volumetric reconstruction of brain activity). In some examples, processor 108 may transmit the correlation maps to controller unit 102, which may use the data included in correlation maps to control various aspects of DCS system 102.

Figure 7:
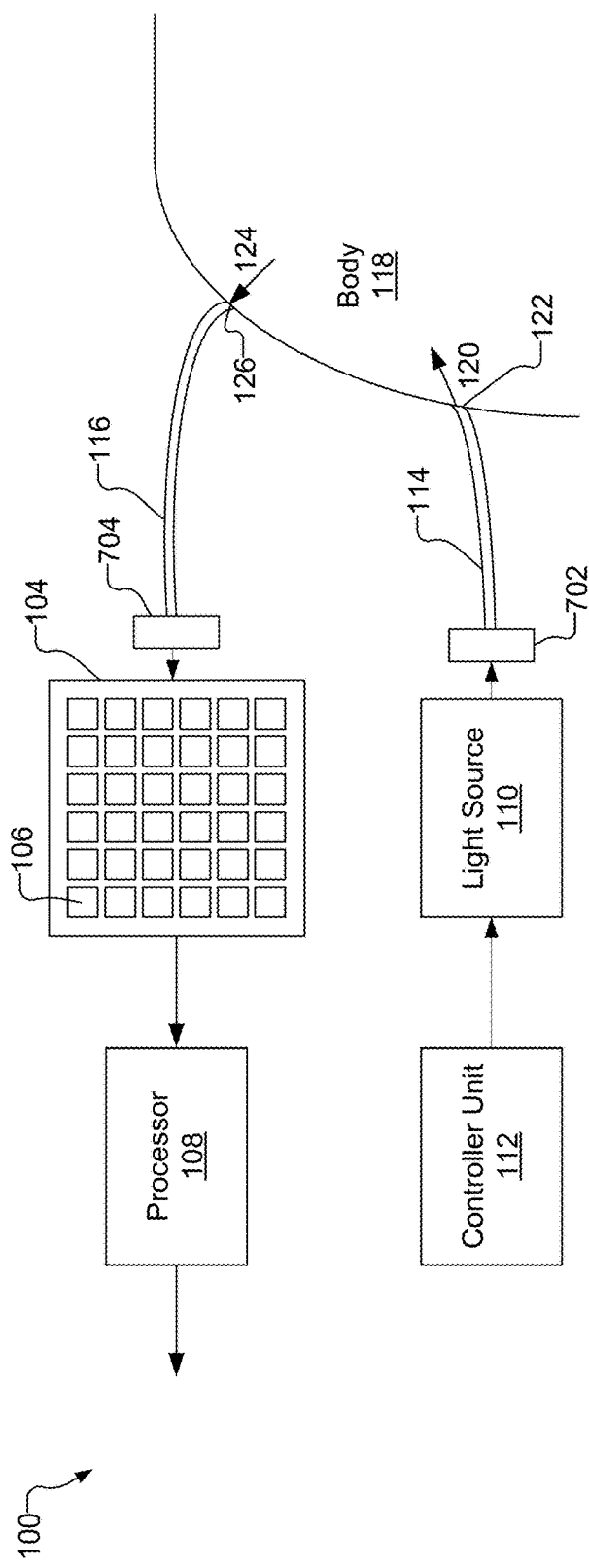
FIG. 7 illustrates an alternative implementation of a DCS system according to principles described herein.

FIG. 7 illustrates an alternative implementation of DCS system 102. FIG. 7 is similar to FIG. 1, except that in FIG. 7, DCS system 102 includes a polarization device 702 and a cross polarizer 704. Polarization device 702 is positioned in an optical path between an output of light source 110 and body 118, and is configured to set a polarization of the light generated by light source 110 to a predetermined state. Cross polarizer 704 is configured to prevent light having the predetermined state from being applied to photodetector array 104. The use of polarization device 702 and cross polarizer 704 may improve the ability to separate signal that arises from the brain as opposed to the scalp and/or skull. This is because light that reflects off the scalp and/or skull likely still has the same polarization state that it had when it was output by light source 110. In contrast, much of the light that enters and emerges from the brain has had its polarization state randomly changed. Hence, by blocking light that has a polarization state that has not changed since being generated by light source 110 from being detected by photodetector array 104, the systems and methods described herein may ensure that the light that is detected by photodetector array 104 has actually entered the brain.

Figure 8:
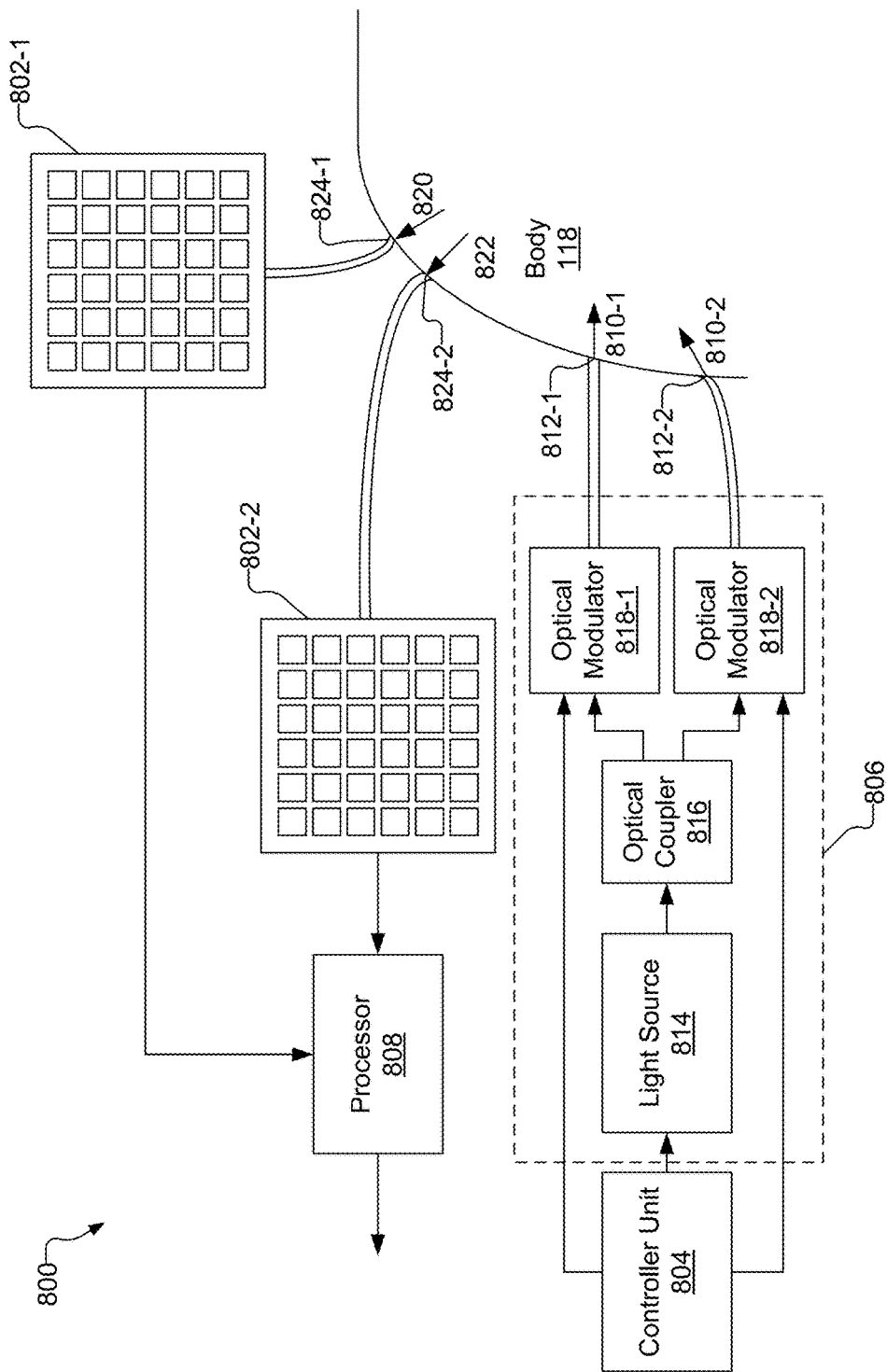
FIG. 8 shows an exemplary DCS system that includes multiple photodetector arrays according to principles described herein.

FIG. 8 shows an exemplary DCS system 800 that includes multiple photodetector arrays 802 (e.g., photodetector array 802-1 and photodetector array 802-1) configured to detect light that exits body 118 at different locations. To facilitate operation of multiple photodetector arrays 802, DCS system 800 includes a controller unit 804 (which may be similar to controller unit 112), a light source assembly 806, and a processor 808 (which may be similar to processor 108).

Light source assembly 806 is configured to generate a first optical beam 810-1 that enters body 118 at a first entry location 812-1 and a second optical beam 810-2 that enters body 118 at a second entry location 812-2. In the example of FIG. 8, light source assembly 806 is implemented by a light source 814 (which may be similar to light source 110), an optical coupler 816, and first and second optical modulators 818-1 and 818-2. Light source 814 is configured to generate a single optical beam. Optical coupler 816 is connected to an output of light source 814 and configured to split the single optical beam into first optical beam 810-1 and second optical beam 810-2.

Optical modulator 818-1 is optically connected to optical coupler 816 and configured to receive optical beam 810-1 and selectively allow optical beam 810-1 to enter body 118 at the first entry location 812-1. Likewise, optical modulator 818-2 is optically connected to optical coupler 816 and configured to receive optical beam 810-2 and selectively allow optical beam 810-2 to enter body 118 at the second entry location 812-2.

As shown, controller unit 804 may be communicatively coupled to optical modulators 818. Controller unit 804 may transmit instructions to optical modulators 818 to cause optical modulators 818 to selectively change the amplitude, phase, and/or polarization state of optical beams 810. In some examples, controller unit 804 may transmit instructions to optical modulator 818-1 that cause optical modulator 818-1 to prevent optical beam 810-1 from entering the body 118 while optical beam 812-2 is entering the body 118. Likewise, controller unit 804 may transmit instructions to optical modulator 818-2 that cause optical modulator 818-2 to prevent optical beam 810-2 from entering the body 118 while optical beam 812-1 is entering the body 118. In this manner, DCS system 800 may ensure that optical beams 810-1 and 810-2 do not interfere one with another.

Photodetector array 802-1 is configured to detect light 820 (e.g., light from either optical beam 810) that exits body 118 at a first exit location 824-1 and output electronic signals representative of the light detected by photodetector array 802-1 as a function of time. Likewise, photodetector array 802-2 is configured to detect light 820 (e.g., light from either optical beam 810) that exits body 118 at a second exit location 824-2 and output electronic signals representative of the light detected by photodetector array 802-2 as a function of time.

Processor 808 is connected to outputs of photodetector arrays 802 and is configured to generate a first correlation map that includes a plurality of spatiotemporal correlation measure values corresponding to the light detected by photodetector array 802-1 and a second correlation map that includes a plurality of spatiotemporal correlation measure values corresponding to the light detected by photodetector array 802-2. This may be performed in any of the ways described herein. The first and second correlation maps (and any other correlation map generated by processor 808 for either photodetector array 802) may be output to a computing device (not shown), which may process the correlation maps in any suitable manner. Likewise, this extension to two photodetector arrays 802 is generalizable to three or more photodetector arrays distributed across the body.

Figure 9:
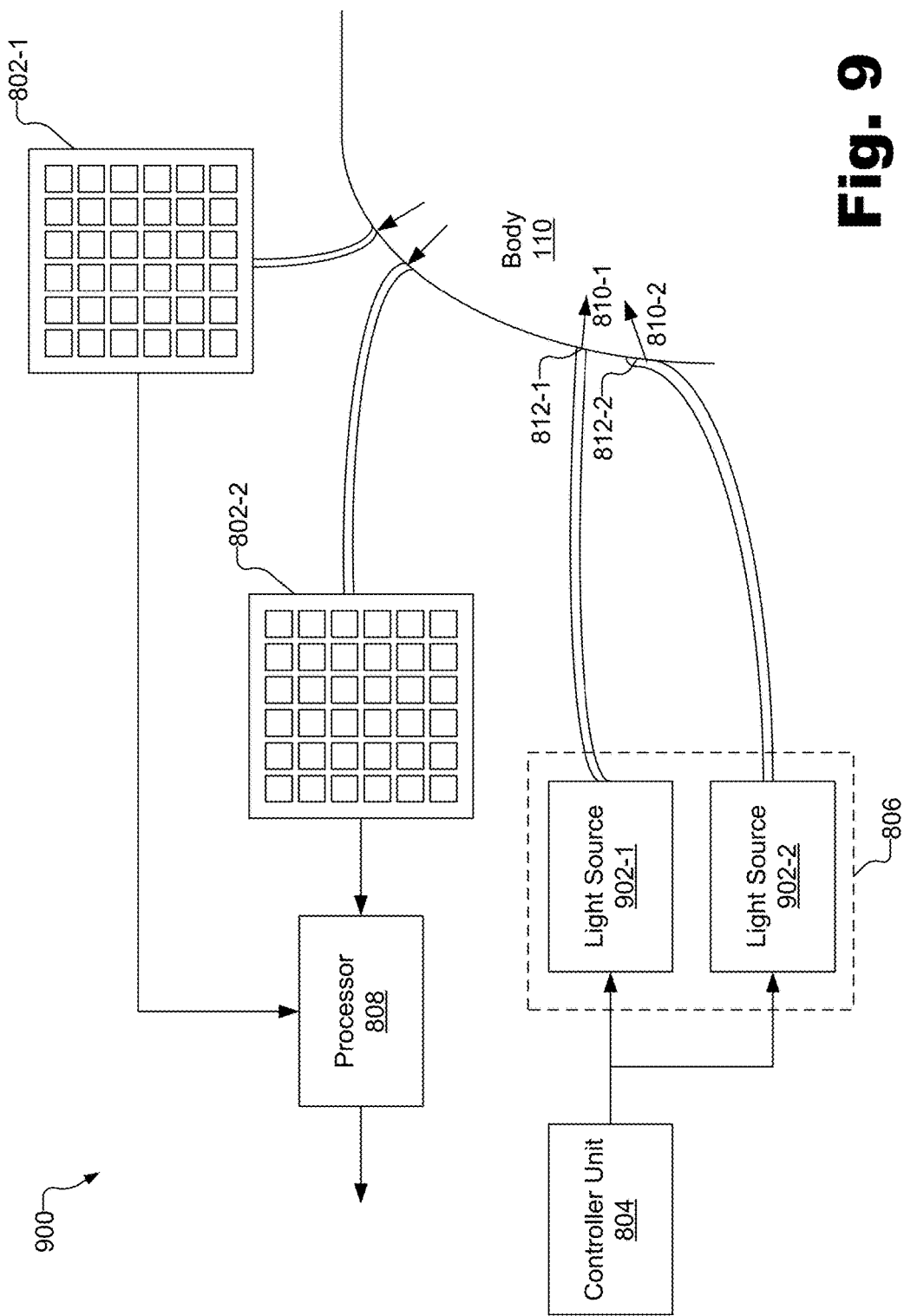
FIG. 9 shows an alternative configuration of the DCS system of FIG. 8 according to principles described herein.

FIG. 9 shows an alternative configuration 900 of DCS system 800. In configuration 900, light source assembly 806 is implemented by multiple light sources 901-1 and 902-2. Light source 902-1 is configured to output optical beam 810-1 and light source 902-2 is configured to output optical beam 810-2. In this configuration, each light source 902 may be controlled by controller unit 804 to output optical beams having different wavelengths and/or other characteristics.

For example, optical beams 810-1 and 810-2 may have different wavelengths. Photodetector arrays 802 may detect this light in series or in parallel and then perform a suitable post-processing step to obtain more information about the decorrelation signal than would be possible from measuring a single wavelength. For example, light sources 902-1 and 902-2 may be turned on one at a time in series and photodetector arrays 802 together with processor 808 may detect the light, digitize the resulting electronic signals, and generate correlation maps for each wavelength. A separate computing device (not shown) may determine a multi-wavelength weighted combination, which may be used to help better isolate decorrelation signal that arises from only scattering changes, as opposed to scattering and absorption and blood flow changes. This extension to two light sources 902 is generalizable to three or more light sources distributed across the body.

Figure 10:
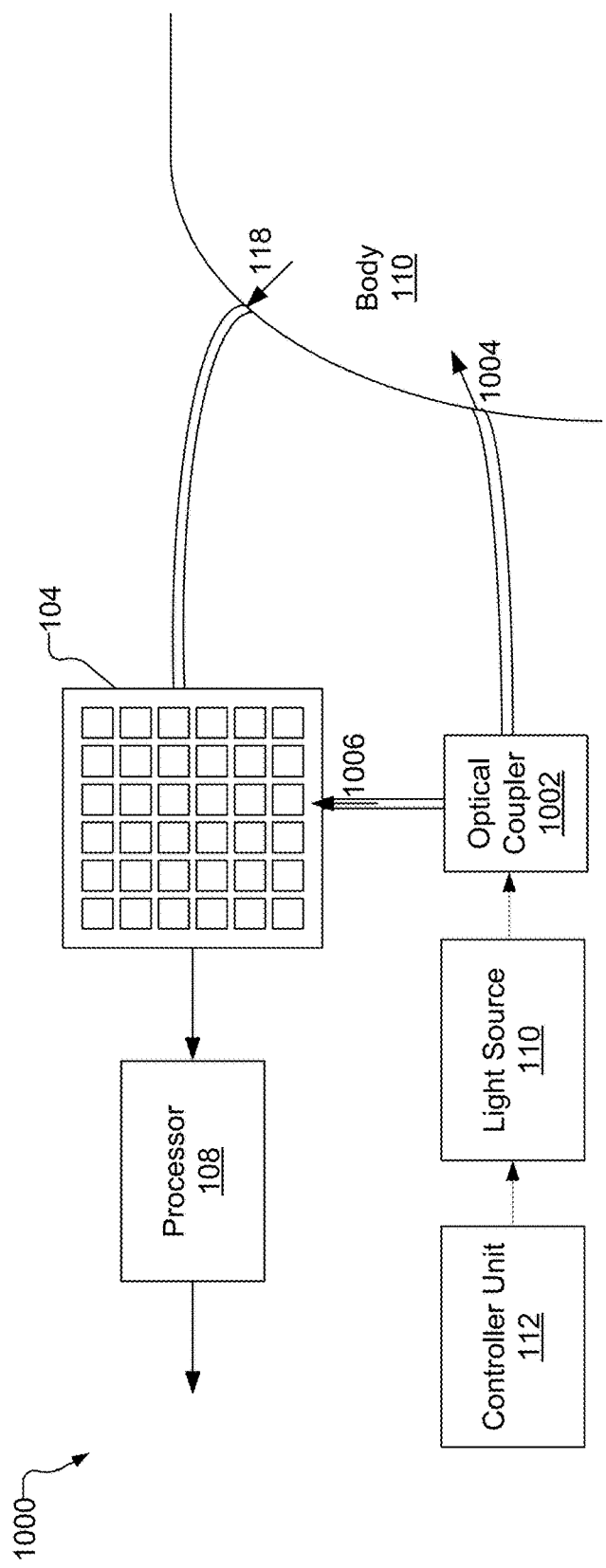
FIG. 10 illustrates an exemplary configuration in which an optical coupler is configured to split an optical beam output by a light source into a sample and reference beam according to principles described herein.

FIG. 10 illustrates an exemplary configuration in which an optical coupler 1002 is configured to split an optical beam output by light source 110 such that a first optical beam 1004 (i.e., a sample beam) enters body 110 and a second optical beam 1006 (i.e., a reference beam) is applied directly to photodetector array 104. Optical beam 1006 may be referred to as a flat reference beam and may be configured to boost a signal level of the light 118 that exits the body 110 above the noise floor so that photodetector array 104 may more easily detect light 118.

In some examples, any of the photodetector arrays describe herein may be included as part of a wearable assembly configured to be positioned on a body of a user. For example, the wearable assembly may be worn on the head of a user.

Figure 11:
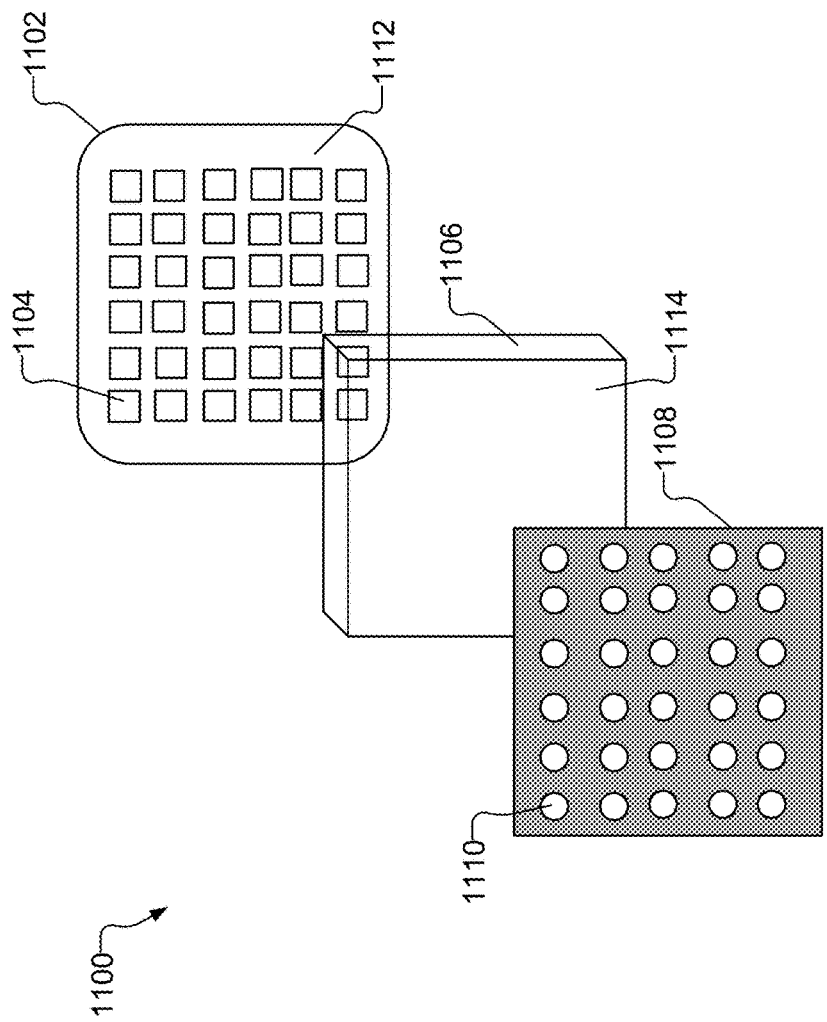
FIG. 11 is an exploded view of an exemplary non-invasive wearable assembly according to principles described herein.

To illustrate, FIG. 11 is an exploded view of an exemplary non-invasive wearable assembly 1100. As shown, wearable assembly 1100 includes a photodetector array 1102 that has a plurality of photodetectors (e.g., photodetector 1104), an optical spacer 1106, and a pinhole array 1108 that has a plurality of pinholes (e.g., pinhole 1110).

Optical spacer 1106 may be implemented by a sheet of glass or other flexible transparent material of finite thickness and may be attached to a front surface 1112 of photodetector array 1102.

Pinhole array 1108 may be made out of any suitable material and may be attached to a front surface 1114 of optical spacer 1106. The pinholes of pinhole array 1108 may be configured to be aligned with the photodetectors of photodetector array 1102. Hence, if photodetector array 1102 is a K by L array that includes K times L photodetectors, pinhole array 1108 is also a K by L array that includes K times L pinholes.

The pinholes of pinhole array 1108 are configured to be in physical contact with the body and allow only a certain amount of light to be incident upon each of the photodetectors in photodetector array 1102. In other words, pinhole array 1108 blocks a certain amount of the speckle pattern from being detected by each of the photodetectors in photodetector array 1102. By blocking light, pinhole array 1108 may reduce the number of speckles that fall upon each photodetector, which may improve the contrast of spatiotemporal correlation.

Figure 12:
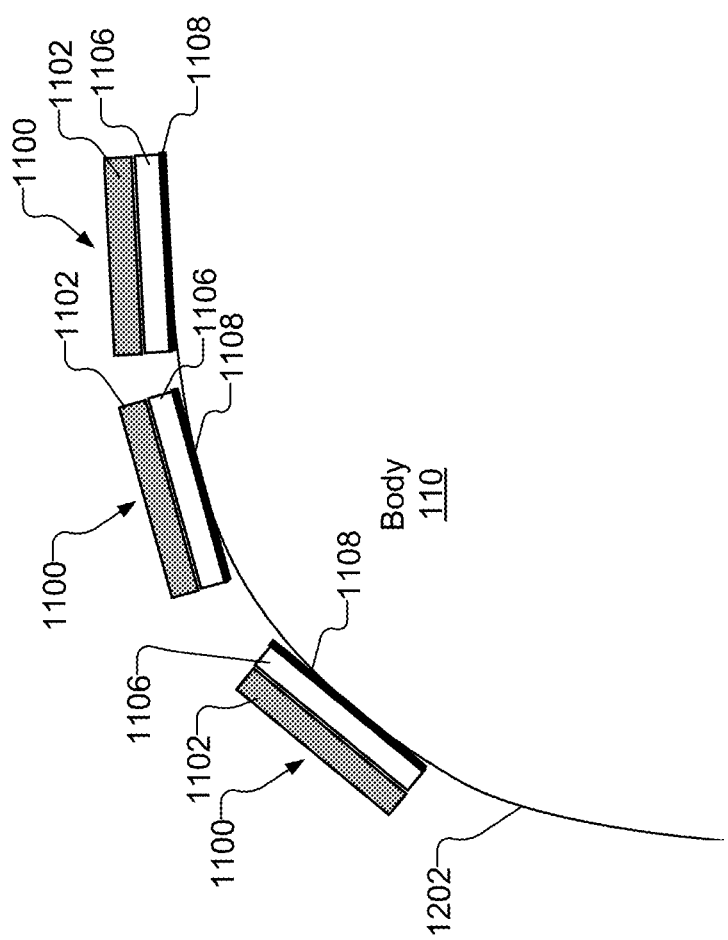
FIG. 12 shows wearable assemblies positioned on an outer surface of a body according to principles described herein.

FIG. 12 shows three wearable assemblies 1100 positioned on an outer surface 1202 of body 110. As shown, in this configuration, there is no need for optical fibers to be included to direct light exiting body 110 to photodetector arrays 1102.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 13:
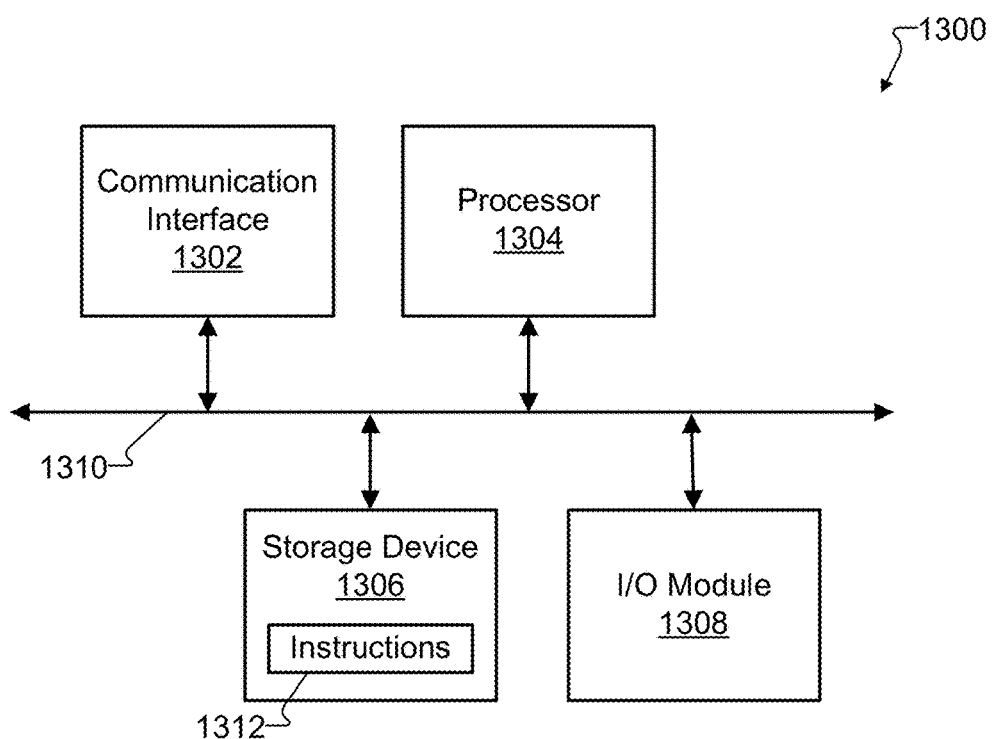
FIG. 13 illustrates an exemplary computing device according to principles described herein.

FIG. 13 illustrates an exemplary computing device 1300 that may be specifically configured to perform one or more of the processes described herein. As shown in FIG. 13, computing device 1300 may include a communication interface 1302, a processor 1304, a storage device 1306, and an input/output ("I/O") module 1308 communicatively connected one to another via a communication infrastructure 1310. While an exemplary computing device 1300 is shown in FIG. 13, the components illustrated in FIG. 13 are not intended to be limiting. Additional or alternative components may be used in other embodiments. Components of computing device 1300 shown in FIG. 13 will now be described in additional detail.

Communication interface 1302 may be configured to communicate with one or more computing devices. Examples of communication interface 1302 include, without limitation, a wired network interface (such as a network interface card), a wireless network interface (such as a wireless network interface card), a modem, an audio/video connection, and any other suitable interface.

Processor 1304 generally represents any type or form of processing unit capable of processing data and/or interpreting, executing, and/or directing execution of one or more of the instructions, processes, and/or operations described herein. Processor 1304 may perform operations by executing computer-executable instructions 1312 (e.g., an application, software, code, and/or other executable data instance) stored in storage device 1306.

Storage device 1306 may include one or more data storage media, devices, or configurations and may employ any type, form, and combination of data storage media and/or device. For example, storage device 1306 may include, but is not limited to, any combination of the non-volatile media and/or volatile media described herein. Electronic data, including data described herein, may be temporarily and/or permanently stored in storage device 1306. For example, data representative of computer-executable instructions 1312 configured to direct processor 1304 to perform any of the operations described herein may be stored within storage device 1306. In some examples, data may be arranged in one or more databases residing within storage device 1306.

I/O module 1308 may include one or more I/O modules configured to receive user input and provide user output. I/O module 1308 may include any hardware, firmware, software, or combination thereof supportive of input and output capabilities. For example, I/O module 1308 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1308 is configured to provide graphical data to a display for presentation to a user. The graphical data may be representative of one or more graphical user interfaces and/or any other graphical content as may serve a particular implementation.

In some examples, any of the systems, computing devices, processors, controller units, and/or other components described herein may be implemented by computing device 1300. For example, processor 108, processor 108, controller unit 112, and/or controller unit 804 may be implemented by processor 1304.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a wearable assembly configured to be positioned on a body and comprising:
a K by L photodetector array comprising a plurality of photodetectors and configured to
detect light that exits the body at a second location after the light enters the body at a first location different than the second location and scatters within the body, and
output a plurality of electronic signals representative of the detected light as a function of time, where each photodetector included in the photodetector array is configured to output a different one of the electronic signals;
an optical spacer attached to a front surface of the photodetector array;
a pinhole array attached to a front surface of the optical spacer, the pinhole array having a K by L array of pinholes configured to be aligned with the photodetectors, the pinhole array configured to be in physical contact with the body and allow a certain amount of light to be incident upon each of the photodetectors; and a processor coupled to an output of the photodetector array and configured to sample the electronic signals output by the photodetector array at a plurality of delay times during a predetermined time period to generate a sequence of frames each corresponding to a different delay time in the plurality of delay times, where each of the frames includes K times L digital sample values at K by L pixel locations that correspond to locations of the photodetectors within the photodetector array, apply a plurality of temporal-based and spatial-based correlation measurement operations to the sample values in each of the frames, generate, based on the application of the temporal-based and spatial-based correlation measurement operations to the sample values in each of the frames, a plurality of spatiotemporal correlation measure values for the light detected by the photodetector array, and include the plurality of spatiotemporal correlation measure values in a correlation map that corresponds to a predetermined delay time interval that represents a difference between two delay times within the plurality of delay times.

2. The system of claim 1, wherein the processor is configured to apply the plurality of temporal-based and spatial-based correlation measurement operations to the sample values in each of the frames by applying the plurality of temporal-based and spatial-based correlation measurement operations to sample values included in a plurality of overlapping pixel regions in each of the frames, where each of the pixel regions includes Px by Py pixel locations, and Px times Py is greater than one; and the plurality of spatiotemporal correlation measure values each correspond to a different one of the overlapping pixel regions.

3. The system of claim 2, wherein:

the predetermined delay time interval is one;

a first pixel region in the overlapping pixel regions includes a first pixel location and a second pixel location;

each of the frames includes a first sample value corresponding to the first pixel location and a second sample value corresponding to the second pixel location;

the frames include a first frame corresponding to a first delay time, a second frame corresponding to a second delay time immediately subsequent to the first delay time, and a third frame corresponding to a third delay time immediately subsequent to the second delay time; and the processor is configured to apply the temporal-based correlation measurement operations by processing the first sample value in the first frame with the first sample value in the second frame to obtain a first temporal correlation measure value for the first pixel location, processing the first sample value in the second frame with the first sample value in the third frame to obtain a second temporal correlation measure value for the first pixel location, processing the second sample value in the first frame with the second sample value in the second frame to obtain a first temporal correlation measure value for the second pixel location, and processing the second sample value in the third frame with the second sample value in the third frame to obtain a second temporal correlation measure value for the second pixel location.

4. The system of claim 3, wherein the processing of the first sample value in the first frame with the first sample value in the second frame to obtain the first temporal correlation measure value for the first pixel location comprises multiplying the first sample value in the first frame with the first sample value in the second frame.

5. The system of claim 3, wherein the processor is configured to apply the spatial-based correlation measurement operations by:

processing the first temporal correlation measure value for the first pixel location with the first temporal correlation measure value for the second pixel location to obtain a first spatial correlation measure; and processing the second temporal correlation measure value for the first pixel location with the second temporal correlation measure value for the second pixel location to obtain a second spatial correlation measure.

6. The system of claim 5, wherein the processing of the first temporal correlation measure value for the first pixel location with the first temporal correlation measure value for the second pixel location comprises computing a variance of the first temporal correlation measure value for the first pixel location and the first temporal correlation measure value for the second pixel location.

7. The system of claim 6, wherein the processor is configured to:

combine the first and second spatial correlation measure values to obtain a single spatiotemporal correlation measure value for the first pixel region; and include the single spatiotemporal correlation measure value in the correlation map at a location that corresponds to the first pixel region.

8. The system of claim 7, wherein the combining of the first and second spatial correlation measure values comprises adding the first and second spatial correlation measure values.

9. The system of claim 7, wherein:

a second pixel region in the overlapping pixel regions includes the second pixel location and a third pixel location;

each of the frames further includes a third sample value corresponding to the third pixel location; and the processor is further configured to apply the temporal-based correlation measurement operations by processing the third sample value in the first frame with the third sample value in the second frame to obtain a first temporal correlation measure value for the third pixel location, and processing the third sample value in the second frame with the third sample value in the third frame to obtain a second temporal correlation measure value for the third pixel location.

10. The system of claim 9, wherein the processor is further configured to apply the spatial-based correlation measurement operations by:

processing the first temporal correlation measure value for the second pixel location with the first temporal correlation measure value for the third pixel location to obtain a third spatial correlation measure; and processing the second temporal correlation measure value for the second pixel location with the second temporal correlation measure value for the third pixel location to obtain a fourth spatial correlation measure.

11. The system of claim 10, wherein the processor is further configured to:
combine the third and fourth spatial correlation measure values to obtain a single spatiotemporal correlation measure value for the second pixel region; and
include the single spatiotemporal correlation measure value for the second pixel region in the correlation map at a location that corresponds to the second pixel region.

12. The system of claim 3, wherein the frames further include a fourth frame corresponding to a fourth delay time immediately subsequent to the third delay time and a fifth delay time immediately subsequent to the fourth delay time, and wherein the processor is further configured to:
generate, based on the application of the temporal-based and spatial-based correlation measurement operations to the sample values in each of the frames, an additional plurality of spatiotemporal correlation measure values for the light detected by the photodetector array; and
include the additional plurality of spatiotemporal correlation measure values in an additional correlation map that corresponds to a predetermined delay time interval equal to two.

13. The system of claim 12, wherein the processor is configured to apply the temporal-based correlation measurement operations to generate the additional correlation map by:
processing the first sample value in the first frame with the first sample value in the third frame to obtain a first temporal correlation measure value associated with the additional correlation map for the first pixel location;
processing the first sample value in the third frame with the first sample value in the fifth frame to obtain a second temporal correlation measure value associated with the additional correlation map for the first pixel location;
processing the second sample value in the first frame with the second sample value in the third frame to obtain a first temporal correlation measure value associated with the additional correlation map for the second pixel location; and
processing the second sample value in the third frame with the second sample value in the fifth frame to obtain a second temporal correlation measure value associated with the additional correlation map for the second pixel location.

14. The system of claim 13, wherein the processor is configured to apply the spatial-based correlation measurement operations to generate the additional correlation map by:
processing the first temporal correlation measure value associated with the additional correlation map for the first pixel location with the first temporal correlation measure value associated with the additional correlation map for the second pixel location to obtain a first spatial correlation measure associated with the additional correlation map; and
processing the second temporal correlation measure value associated with the additional correlation map for the first pixel location with the second temporal correlation measure value associated with the additional correlation map for the second pixel location to obtain a second spatial correlation measure associated with the additional correlation map.

15. The system of claim 14, wherein the processor is further configured to:
combine the first and second spatial correlation measure values associated with the additional correlation map to obtain a single spatiotemporal correlation measure value associated with the additional correlation map for the first pixel region; and
include the single spatiotemporal correlation measure value associated with the additional correlation map in the additional correlation map at a location that corresponds to the first pixel region.

16. The system of claim 1, wherein the light that enters the body has a coherence length of at least 5 centimeters.

17. The system of claim 1, further comprising a light source configured to generate the light that enters the body.

18. The system of claim 17, wherein the light source is a high-coherence laser diode.

19. The system of claim 17, further comprising a polarization device positioned in an optical path between an output of the light source and the body, the polarization device configured to set a polarization of the light generated by the light source to a predetermined state.

20. The system of claim 19, further comprising a cross polarizer positioned between an optical path from the body to the photodetector array, the cross polarizer configured to prevent light having a polarization of the predetermined state from being applied to the photodetector array.

21. The system of claim 17, further comprising a single-mode optical fiber configured to be connected to an output of the light source and to the body at the first location, wherein the light generated by the light source travels to the body by way of the single-mode optical fiber.

22. The system of claim 17, further comprising a controller unit configured to control the light source by:
turning on and off the light source; and
setting an intensity of the light generated by the light source.

23. The system of claim 17, further comprising an optical coupler connected to an output of the light source, the optical coupler configured to split the light into a first optical beam that enters the body at the first location and a second optical beam that is applied directly to the photodetector array, the second optical beam configured to boost a signal level of the light that exits the body at the second location.

24. The system of claim 1, further comprising a multi-mode optical fiber configured to be connected to the body at the second location and to an input of the photodetector array, wherein the light that exits the body at the second location travels to the photodetector array by way of the multi-mode optical fiber.

25. The system of claim 1, wherein the photodetectors are single photon avalanche diode (SPAD) circuits.

26. The system of claim 1, wherein the predetermined time period is less than or equal to one microsecond.

27. The system of claim 1, wherein the sequence of frames comprises between 10 frames and 100,000 frames.

28. The system of claim 1, wherein the body is a head of a patient.

* * * * *